United States Patent [19]

Gabriel

[11] Patent Number: 4,823,906
[45] Date of Patent: Apr. 25, 1989

[54] STETHOSCOPE HAVING A BODY CONTACT PIECE PROVIDED WITH TWO ALTERNATIVELY EMPLOYED AUSCULTATION HEADS

[75] Inventor: Jochen Gabriel, Stuttgart, Fed. Rep. of Germany

[73] Assignee: Wilhelm Haselmeier GmbH & Co., Stuttgart, Fed. Rep. of Germany

[21] Appl. No.: 826,137

[22] Filed: Feb. 4, 1986

[30] Foreign Application Priority Data

Feb. 21, 1985 [DE] Fed. Rep. of Germany ... 8504877[U]

[51] Int. Cl.⁴ .............................................. A61B 7/02
[52] U.S. Cl. ..................................... 181/137; 181/131
[58] Field of Search ................................ 181/131, 137

[56] References Cited

U.S. PATENT DOCUMENTS

| | | | |
|---|---|---|---|
| 1,671,936 | 5/1928 | Rieger | 181/137 |
| 3,035,656 | 5/1962 | Kebel | 181/137 |
| 3,193,047 | 7/1967 | Allen | 181/137 |
| 3,712,409 | 1/1973 | Kizakisz et al. | 181/137 |
| 3,938,615 | 2/1976 | Bodenger | 181/137 X |

FOREIGN PATENT DOCUMENTS

| | | |
|---|---|---|
| 504509 | 10/1979 | Australia . |
| 1267378 | 5/1968 | Fed. Rep. of Germany . |
| 2204730 | 8/1972 | Fed. Rep. of Germany . |
| 2309416 | 9/1974 | Fed. Rep. of Germany . |
| 2631154 | 3/1977 | Fed. Rep. of Germany . |
| 1504079 | 3/1978 | United Kingdom . |

Primary Examiner—Benjamin R. Fuller
Attorney, Agent, or Firm—Theodore J. Koss, Jr.

[57] ABSTRACT

A double-headed body contact piece has first and second acoustic connector portions connected to first and second acoustic passages of a stethoscope-tube attachment, and further has a first, non-differential auscultation head with a single auscultation chamber and a second, differential-auscultation head with a pair of chambers which latter are to be placed simultaneously with each other against a patient's body with a predetermined spacing between them. A switchover mechanism has first and second settings, involving registration and non-registration of various passages internal to the body contact piece. In the first setting, acoustic connections are established leading from the single chamber of the first head to both the first and the second acoustic connector portions, these two connections being of at least equivalent geometry and having the same dimensions so as to be acoustically equivalent to each other. In the second setting, one acoustic connection is established leading from one chamber of the second head to one of the acoustic connector portions, and another connection is established leading from the second head's other chamber to the other acoustic connector portion, these two connections likewise being of at least equivalent geometry and having the same dimensions so as to be acoustically equivalent to each other. In the first setting, the physician uses the first head and hears identical body sounds in his two earpieces. In the second setting, he uses the second head and hears in his two earpieces body sounds as picked up by one and by the other of the second head's two chamber, for differential auscultation.

38 Claims, 4 Drawing Sheets

STETHOSCOPE HAVING A BODY CONTACT PIECE PROVIDED WITH TWO ALTERNATIVELY EMPLOYED AUSCULTATION HEADS

BACKGROUND OF THE INVENTION

Stethoscopes are known having a double-headed body contact piece provided at one axial end thereof with a larger-diameter auscultation head and provided at the other axial end thereof with a smaller-diameter auscultation head. Typically, one head is for example used for auscultation of lower-frequency body sounds and the other for auscultation of higher-frequency body sounds.

In configurations where the body contact piece is provided with first and second acoustic connector portions which are respectively in acoustic communication with the first head and with the second head, the examining physician when he wishes to switch over from one auscultation head to the other can disconnect the stethoscope-tube attachment from one of the body contact piece's two acoustic connector portions and connect the tube attachment instead to the other acoustic connector portion, although this is of course inconvenient. The stethoscope-tube attachment may be of the single-acoustic-passage type leading from the selected acoustic connector portion of the body contact piece to a single earpiece which the physician wears on one ear during auscultation. Or else, a two-acoustic-passage stethoscope-tube attachment can be employed. The two acoustic-signal-transmitting passages of the latter are for example connected to the selected one of the body contact piece's two acoustic connector portions by means of a Y-type stethoscope-tube portion or by means of a Y-type connector fixture; the two acoustic-signal-transmitting passages of the stethoscope-tube attachment are then typically connected at their other ends to respective ones of the two earpieces of a binaural headset.

A further possibility is to provide the body contact piece with a single acoustic connector portion which acoustically communicates, internally of the body contact piece, with the ausculation chamber of a selected one of the two auscultation heads, the selection of one head or the other being performed by means of a manually activated switchover mechanism. In such case the body contact piece's single acoustic connector portion can, as before, be connected to a single-acoustic-passage stethoscope-tube attachment leading to a single earpiece, or can be connected via a Y-type tube portion or Y-type connector fixture to the two passages of a two-acoustic-passage stethoscope-tube attachment whose two acoustic-signal-transmitting passages lead to respective ones of the two earpieces of a binaural headset.

West German published patent application ("Offenlegungsschrift") No. 2 204 730 discloses a modification of the configuration set forth immediately above. Instead of the body contact piece having a single acoustic connector portion which acoustically communicates, internally of the body contact piece, with the selected one of the two auscultation heads, the body contact piece is provided with two acoustic connector portions, each connected to a respective passage of a two-acoustic-passage stethoscope-tube attachment. However, the two acoustic connector portions on the body contact piece are, internally of the latter, acoustically connected to each other. Accordingly, the use of two acoustic connector portions instead of a single acoustic connector portion merely serves to establish a conventional Y-junction for the two stethoscope-tube passages, namely now internally of the body contact piece, instead of establishing such Y-junction externally thereof by means of the conventional Y-type tube portion or Y-type connector fixture.

SUMMARY OF THE INVENTION

It is a main object of the invention to provide a stethoscope having a double-headed body contact piece that is provided with an internal switchover mechanism of fundamentally different acoustical configuration than in the prior art.

In accordance with the invention the double-headed body contact piece of the stethoscope is provided with two acoustic connector portions, each connected or connectable to a respective acoustic-signal-transmitting passage of a two-acoustic-passage stethoscope-tube attachment. Furthermore, the body contact piece is provided with an externally activatable internal switchover mechanism which is designed in such a manner that, in one setting, it causes two distinguishable acoustic output signals to be produced, one such signal at one acoustic connector portion and the other such signal at the other acoustic connector portion, with these two distinguishable acoustic output signals being both furnished from one of the two heads of the double-headed body contact piece.

This configuration for the internal switchover mechanism of the body contact piece can be of particular advantage if one of the latter's two auscultation heads is a differential-auscultation head, for example a two-chamber auscultation head. In that event, when the switchover mechanism is moved to the setting which selects the differential-auscultation head, a first acoustic output signal is produced at the first acoustic connector portion of the body contact piece, furnished from one chamber of the differential head; and a distinguishable second acoustic output signal is produced at the other acoustic connector portion of the body contact piece, furnished from the differential head's other chamber. These two distinguishable acoustic signals are then transmitted via respective acoustic-signal-transmitting passages of a two-acoustic-passage stethoscope-tube attachment.

The other head of the double-headed body contact piece can for example be a non-differential auscultation head. In that event, the internal switchover mechanism of the body contact piece can be so designed that the two acoustic passages of the stethoscope-tube attachment receive identical acoustic output signals at both acoustic connector portions of the body contact piece.

The differential-auscultation head may for example be the larger-diameter head of the double-headed body contact piece, and the non-differential auscultation head may be the smaller-diameter head thereof.

Preferably, the internal switchover mechanism of the stethoscope's body contact piece is a rotary mechanism that can be manually rotated from the exterior of the body contact piece. Such a configuration for the switchover mechanism is simple to operate manually and is very sturdy. Also, such a design is ergonomically advantageous, and the exterior of the body contact piece can for example be provided with simple markings or indicia to indicate the present setting of the switchover mechanism.

Preferably, the rotatable switchover mechanism has a planar axial end surface which is in sliding contact with the planar axial end surface of one of the two auscultation heads, or in sliding contact with the planar axial end surface of an intermediate member connected with one of the two heads. With such a configuration, the establishment and disestablishment of the various internal acoustical connections can be accomplished by registration or non-registration of acoustic passages which are provided in the rotary switchover mechanism and in such head or intermediate member and which extend to the plane of said planar axial end surfaces. Such a design tends to simplify the geometry of the acoustic connections established at such plane and, as a result, tends to greatly reduce losses in the strength or energy of the acoustic signals to be transmitted. Loss of signal strength or energy also tends to be minimized if the two acoustic connector portions for the stethoscope-tube attachment are provided on the rotating switchover mechanism, because the latter is located axially in between the two auscultation heads.

In a particularly preferred embodiment of the invention, the switchover mechanism has at least one first setting and at least one second setting. When the first setting is selected then, by means of passages internal to the body contact piece, the resulting acoustic connection leading from the single chamber of the non-differential head to the first acoustic connector portion, and the acoustic connection leading from the same chamber of the same head to the second acoustic connector portion, have geometries which are identical or else at least equivalent to each other (e.g. are mirror-symmetrical to each other) and furthermore have the same dimensions, so that these two acoustic connections be acoustically equivalent to each other. Likewise, when the second setting is selected, the resulting acoustic connecting leading from one of the two chambers of the differential-auscultation head to the first acoustic connector portion, and the acoustic connection leading from the other chamber of the differential head to the other acoustic connector portion, have geometries which are identical or at least equivalent to each other (e.g. mirror-symmetrical to each other) and furthermore have the same dimensions, so that these two acoustic connections likewise be acoustically equivalent to each other.

Further advantageous features of the invention will best be understood from the following description of a preferred embodiment when considered in conjunction with the accompanying drawing, and are also set forth in various ones of the dependent claims. It is noted that the preferred embodiment shown and described herein is offered merely in the sense of a concrete embodiment of the inventive concepts and for purposes of explanation and is not to be understood as constituting the only stethoscope design encompassed within the scope of the present invention.

DESCRIPTION OF THE PREFERRED EMBODIMENT

Figure 1:
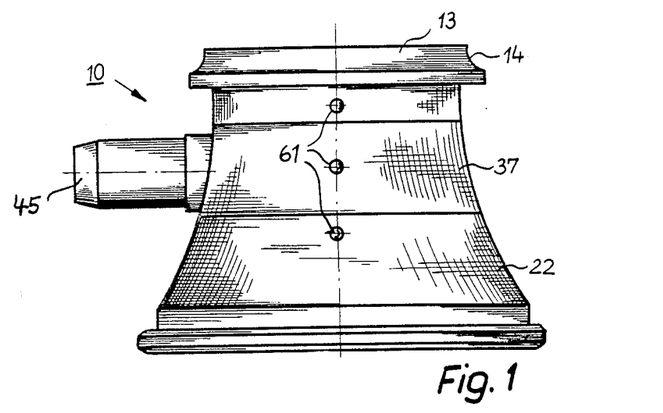
FIG. 1 is a side view of the body contact piece of an exemplary embodying the present invention.
Figure 2:
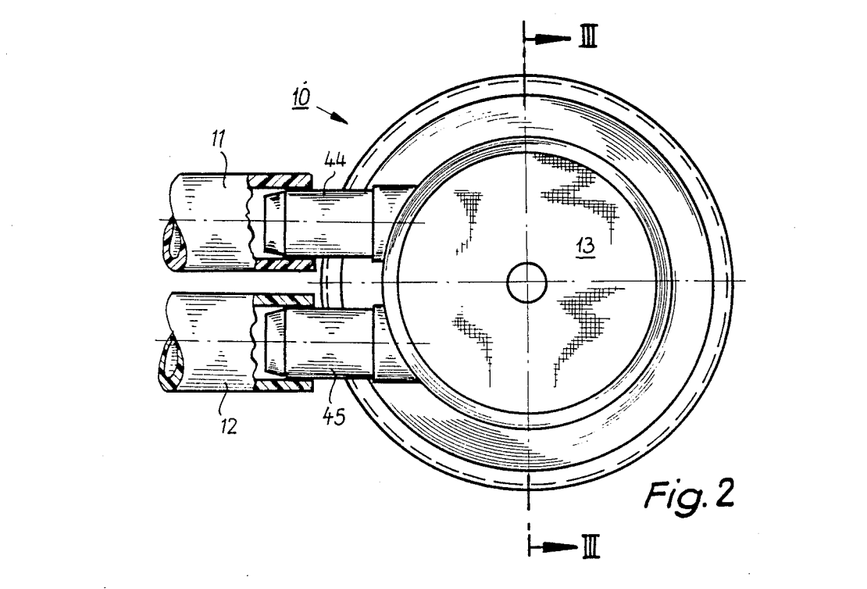
FIG. 2 is a top view looking down upon the body contact piece of FIG. 1, the two-acoustic-passage stethoscope-tube attachment be visible in this view.
Figure 3:
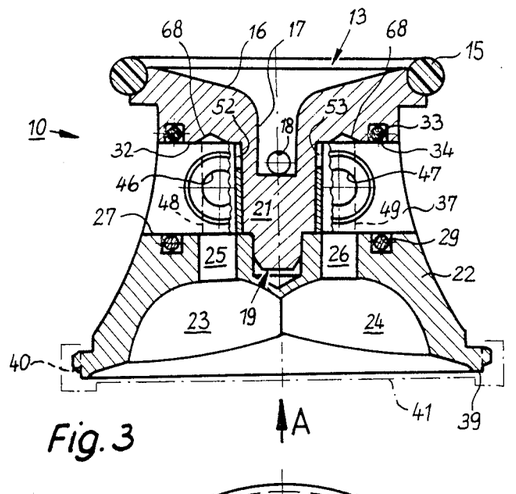
FIG. 3 is a sectional view through the body contact piece, the section being taken along line III—III of FIG. 2, the switchover mechanism of the stethoscope being in part shown not sectioned.

FIGS. 1–3 depict the body contact piece of a stethoscope in accordance with the invention. As shown best in FIG. 2, the body contact piece 10 is acoustically connected to the two acoustic passages of a two-acoustic-passage stethoscope-tube attachment 11, 12. At the other end of stethoscope-tube attachment 11, 12 the latter's two acoustic passages are each acoustically connected to a respective one of the two earpieces of a (non-illustrated) binaural headset.

Figure 5:
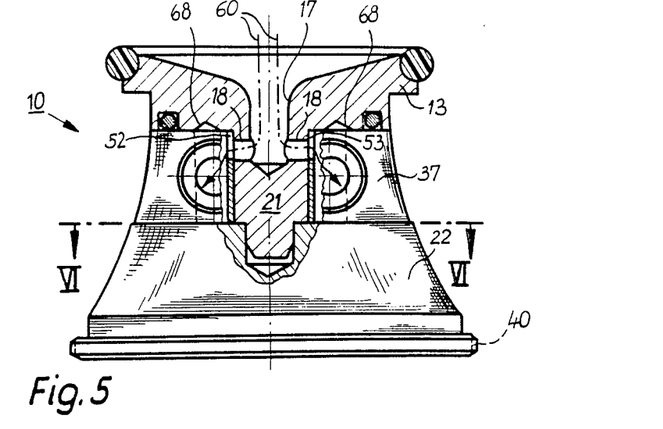
FIG. 5 is a analogous to FIG. 3, but showing the switchover mechanism in a setting thereof different from the one shown in FIG. 3.

The body contact piece 10 includes a first, non-differential auscultation head 13 of smaller diameter at whose outer periphery is provided an annular groove 14 in which an O-ring 15 is secured, in order to be able to press the contact piece against the surface of a patient's body in sound-tight manner. The acoustic chamber 16 of this first auscultation head 13 merges into a central passage 17 from which latter, as shown in FIG. 5, two lateral passages 18 branch off. These two lateral passages 18 extend radially outwards through to the outer periphery of a cylindrical head-interconnecting portion 21. The latter near its bottom end 19 (FIG. 3) is permanently connected, e.g. by press-fitting, to a larger-diameter, second, differential-auscultation head 22, in order to establish a fixed relationship between the angular position of the smaller-diameter first head 13 and the angular position of the larger-diameter second head 22.

Figure 4:
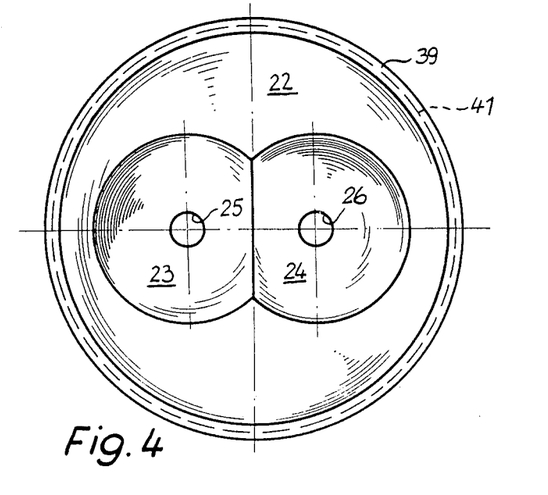
FIG. 4 is an axial end view of the body contact piece, seen in the direction of arrow A in FIG. 3.
Figure 6:
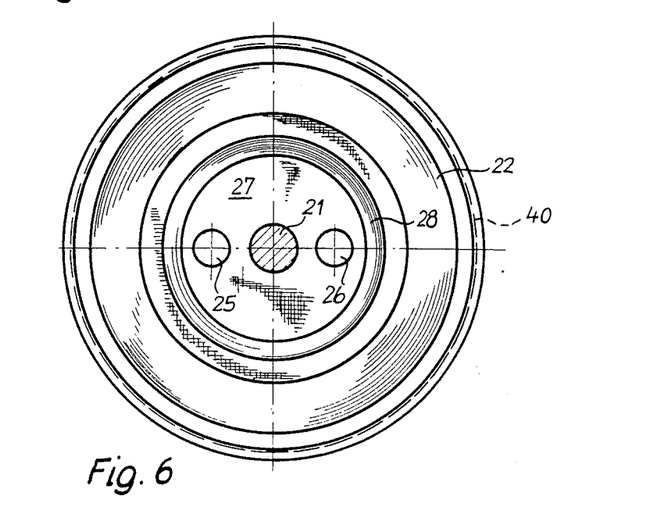
FIG. 6 is a sectional view taken along section line VI—VI of FIG. 5.
Figure 7:
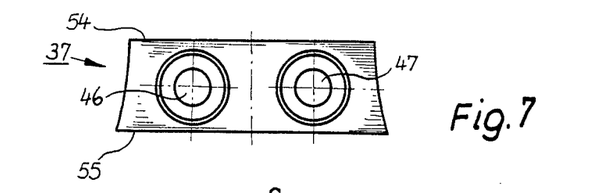
FIG. 7 is a side view of the switchover mechanism's rotary switchover member, shown facing out of the picture plane with the same orientation as in FIGS. 3 and 5, and viewed in the direction of arrow B of FIG. 8.

As shown in FIGS. 3 and 4, the second, differential-auscultation head 22 has two spherical or paraboidal acoustic chambers 23, 24, whose geometric centers or foci are spaced from each other more than ten millimeters. The two acoustic chambers 23, 24 of the larger-diameter, differential-auscultation head 22 pick up body sounds from two distinguishable auscultation locations. The shapes and arrangement of the two chambers 23, 24 are pictorially defined in FIGS. 3 and 4 and, inasmuch as differential-auscultation heads are in themselves well known in the art, need not be described in further detail herein. Acoustic-signal-transmitting passages 25, 26 lead from respective ones of the two acoustic chambers 23, 24 to a planar control surface 27 (FIG. 6) constituted by the back axial end face of second auscultation head 22. Control surface 27 is in addition provided with an annular groove 28 which accommodates an O-ring 29 made of polytetrafluoroethylene (PTFE). Similarly, the planar back axial end face 32 of first auscultation head 13 is provided with an annular groove 33 which accommodates an O-ring 34 made of PTFE. It will be understood that the grooves 28, 33 could be of other, i.e. non-circular, shapes. The O-rings 29, 34 serve chiefly to make the rotary sliding action of the axial end faces of an annular switchover member 37 between and against the two axial end surfaces 27 and 32 as low-friction and greased-seeming as possible. In addition, the O-rings 29, 34 prevent undesirable penetration of ambient sound into the interior of the auscultation heads and, conversely, prevent acoustic signal energy within the auscultation heads from escaping to the exterior as lost signal energy. The differential-auscultation head 22 is threaded at it external periphery so that a conventional diaphragm carrier with a diaphragm 41 can be screwed onto the head's front axial end. Additionally, the front axial end of head 22 is provided with an annular, planar support surface 39 for the diaphragm 41, to help retain the shape of the latter and prevent diaphragm deformation.

Figure 8:
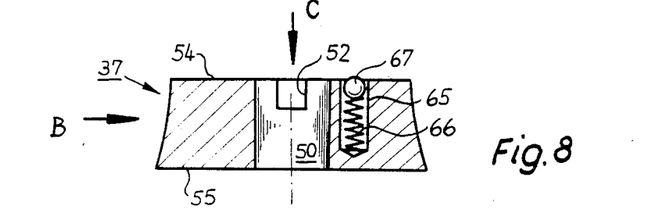
FIG 8 is a sectional view, taken along section line VIII—VIII of FIG. 9.
Figure 9:
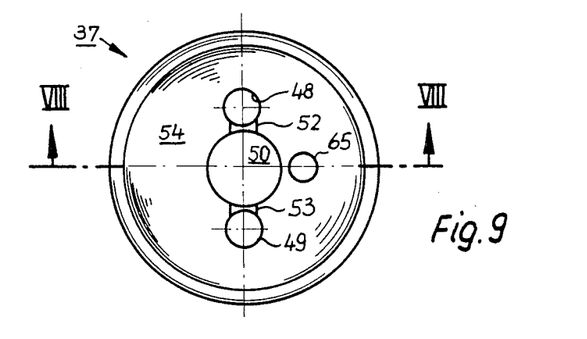
FIG. 9 is a top axial end view of the rotary switchover member, as seen in the direction of arrow C of FIG. 8.

The rotary switchover member 37 is shown in detail in FIGS. 7–10. It is provided with first and second internally threaded, multi-diameter acoustic connector portions 46, 47 (FIGS. 7 and 10), the first and second acoustic connector portions 46, 47 receiving respective screwed-in tube connectors 44, 45 (see FIG. 2) and at their inward, smaller-diameter ends having the form of acoustic passages internal to the switchover member 37. These open into respective ones of two diametrically opposite axial passages 48, 49, communicating with the latter at a location roughly midway between the two axial end faces of the switchover member 37. The two axial passages 48, 49 extend all the way through from the one axial end face 54 to the other axial end face 55 of the switchover member 37, parallel to a cylindrical, central passage 50 internal to member 37. The diameter of central passage 50 approximately corresponds to the external diameter of the earlier-mentioned head-interconnecting portion 21, with the annular switchover member 37 being mounted on the head-interconnecting portion 21 in a manner permitting relative rotation between portion 21 and member 37. When such relative rotation is performed, the earlier-mentioned axial end faces, sliding in rotary fashion over each other, serve as control or valve surfaces As shown in FIGS. 8 and 9, the through-passages 48, 49 communicate with central passage 50 via the intermediary of respective ones of the two short, radial passages 52 and 53. The angular width of each of the two radial passages 52, 53, measured at the periphery of central passage 50, is approximately 30°. As can be seen in FIG. 9, the two short radial passages 52, 53 extend radially to join the central internal passage 50 with the two through-passages 48, 49. Likewise as shown in FIG. 9, each radial passage 52 or 53 is provided in the form of a surface recess in the axial end face 54 of switchover member 37, being recessed into such surface by an axial distance equal (as shown in FIG. 8) to a fraction of the axial length of the central internal passage 50, in this example approximately one-third the axial length of passage 50.

FIG. 3 depicts the body contact piece with the jointly rotatable auscultation heads 13, 22 in one angular setting relative to the switchover member 37. In this angular setting, the two diametrically opposite, radially extending passages 18 in head-interconnecting portion 21 do not register with the two diametrically opposite, radially extending passages 52, 53 in switchover member 37. In this setting, the diameter joining the two passages 18 is located perpendicular to the diameter joining the two passages 52, 53, and the radially outer ends of the two passages 18 of head-interconnecting portion 21 are sealed closed by the peripheral surface of the central passage 50 of switchover member 37. As a result, no acoustic connection is established between the auscultation chamber 16 of smaller-diameter head 13 and the acoustic connector portions 46, 47.

Figure 10:
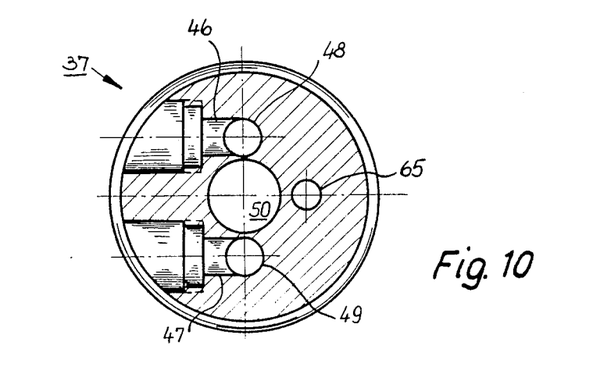
FIG. 10 is a sectional view through the switchover member, taken along a sectioning plane that is parallel to and approximately midway between the two axial end faces of the switchover member.

On the other hand, in this FIG. 3 setting, each of the two chambers 23, 24 of larger-diameter head 22 is acoustically connected to a respective one of the two acoustic connector portions 46, 47, as follows: Axial passage 25 in head 22 register with the axial passage 48 in switchover member 37, these two axial passages being of substantially identical diameter, thereby establishing communication between chamber 23 and passage 48. Axial passage 48, in turn (and as shown in FIG. 10) is permanently in acoustic communication with the acoustic connector portion 46 of switchover member 37, the acoustic connector portion 46 being in permanent communication with stethoscope-tube end portion 11 (compare FIG. 2). Similarly, axial passage 26 in larger-diameter head 22 registers with axial passage 49 of switchover member 37, thereby connecting the chamber 24 to passage 49, and (as shown in FIG. 10), axial passage 49 of switchover member 37 is in permanent communication with acoustic connector portion 47 of member 37, portion 47 being in permanent communication with stethoscope-tube end portion 12.

In this way, the examining physician hears in one of his two earpieces the body sounds as picked up by chamber 23, whereas in his other earpiece the body sounds as picked up by chamber 24, so that the two-chamber head 22 enables him to perform a differential auscultation.

FIG. 5 depicts the body contact piece with the jointly rotatable auscultation heads 13, 22 shown in a different angular setting relative to the switchover member 37. In this angular setting, the two diametrically opposite, axially extending passages 25, 26 of larger-diameter head 22 are not in register with the two axially extending, diametrically opposite passages 48, 49 in switchover member 37; instead the axial passages 25, 26 of head 22 are sealed closed at their rear ends by the axial end face 55 of switchover member 37 (numeral 55 is shown in e.g. FIG. 8). On the other hand, in this FIG. 5 setting, the two radially extending, diametrically opposite passages 18 in head-interconnecting portion 21 register with respective ones of the two short radially extending, diametrically opposite passages 52, 53 of switchover member 37, thus establishing an acoustic connection between chamber 16 of head 13 and the control passages 52, 53. Because the passages 52, 53 (as shown in FIG. 9) permanently communicate with the two axial passages 48, 49 in switchover member 37, and because the two axial passages 48, 49 are in permanent communication with the acoustic connector portions 46 and 47, it follows that the chamber 16 of auscultation head 13 is now in acoustic communication with both stethoscope-tube end portions 11 and 12 (shown in FIG. 2). In this situation, the examining physician hears the body sounds picked up by chamber 16 in both his two earpieces, and identically in the two earpieces, i e., without any differential action. In FIG. 5, the two arrows 60 indicate how the self-same body sounds picked up by chamber 16 are split and pass through the lateral passages 18, then through the short radially extending passages 52, 53, from there into the two axially extending through-passages 48, 49 (shown only by broken lines), and from the latter to the two acoustic connector portions 46, 47 (compare FIG. 7) of switchover member 37.

In this way, depending upon the angular setting of the jointly rotatable auscultation heads 13, 22 and the switchover member 37 relative to each other, there is established, either.

(1) an acoustic connection leading from the single chamber 16 of the first, non-differential head 13 to the first acoustic connector portion 46, and another acoustic connection leading from the same head chamber 16 to the second acoustic connector portion 47; or (2) an acoustic connection leading from one chamber 23 of the pair of chambers 23, 24 of the second, differential-auscultation head 22 to the first acoustic connector portion 46, and another acoustic connection leading from the other chamber 24 of the head 22 to the second acoustic connector portion 47.

In the illustrated embodiment it is particularly advantageous that the two acoustic connections set forth at (1) above are, although not geometrically identical, at least geometrically equivalent to each other and, furthermore, have the same dimensions so as to be acoustically equivalent to each other. Likewise, the two acoustic connections set forth at (2) above are, although not geometrically identical, at least geometrically equivalent to each other and, furthermore, have the same dimensions so as to be likewise acoustically equivalent to each other.

This is achieved in the illustrated embodiment because the two acoustic connections set forth at (1) above are mirror-symmetrical to each other with respect to a symmetry plane that (as considered in e.g. FIG. 10) is a horizontal diametral plane (i.e. a diametral plane which is located equidistant between the two acoustic connector portions 46, 47. Likewise, the two acoustic connections set forth at (2) above are mirror-symmetrical to each other with respect to this symmetry plane.

It will be understood, however, that such acoustic equivalence can be established by an arrangement of internal passages different from the particular arrangement of internal passages employed in the particular embodiment described and shown herein.

As indicated in FIG. 1, indicia 61 can be provided on the body contact piece 10 to indicate to the user which of the two heads 13, 22 is presently in acoustic communication with the two tube end portions 11, 12. However, in actual use, the physician will often place the desired one of the two heads 13, 22 against the surface of the patient's body and then, without considering the indicia 61, will merely rotate the switchover member 37 until he begins to hear body sounds. To facilitate selection of settings, the switchover member 37 can click into place in any of four different angular settings. The click action is achieved by means of a blind bore 65 (see FIG. 8) provided in switchover member 37, the bore 65 accommodating a click ball 67 biased by a spring 66. The back axial end face 32 of the non-differential head 13 is provided with four recesses 68 spaced one from the next by 90°, two of these recesses 68 being visible in each of FIGS. 3 and 5. When switchover member 37 is rotated to one of its four possible angular settings, spring-biased click ball 67 enters into the corresponding recess 68 and with a definite but limited force resists further rotation of member 37.

Summarizing, in the exemplary embodiment illustrated herein, the switchover member 37, in combination with (see FIG. 8) the blind bore 65 formed therein and containing the biasing spring 66 for the click ball 67, constitutes a switchover mechanism. Switchover mechanism 37, 65-67 is operative for establishing acoustic connections from predetermined ones of the auscultation chambers 16 and 23, 24 to the acoustic connector portions 46, 47; for acoustically isolating the acoustic connector portions 46, 47 from predetermined ones of the auscultation chambers 16 and 23, 24; and for acoustically isolating each chamber 23 and 24 of the pair of chambers 23, 24 of the second head 22 from the single chamber 16 of the first head 13. More particularly, in the exemplary embodiment depicted herein, switchover mechanism 37, 65-67 has two settings. In its first setting, the switchover mechanism establishes acoustic connections (from 17 to 18 to 52 to 48; and also, from 17 to 18 to 53 to 49) from the single chamber 16 of the first, non-differential auscultation head 13 to both the first and the second acoustic connector portions 46, 47, while acoustically isolating the single chamber 16 of the first auscultation head 13 from each one of the pair of chambers 23, 24 of the second auscultation head 22. In contrast, in its second setting, switchover mechanism 37, 65-67 establishes an acoustic connection (between 25 and 48) from one chamber 23 of the pair of chambers 23, 24 of the second auscultation head 22 to one acoustic connector portion 46 of the two acoustic connector portions 46, 47 and an acoustic connection (between 26 and 49) from the other chamber 24 of the pair of chambers 23, 24 of the second head 22 to the other acoustic connector portion 47 of the two acoustic connector portions 46,47, while acoustically isolating each one of the pair of chambers 23, 24 of the second head 22 from the single chamber 16 of the first auscultation head 13.

It will be understood that each of the elements described above, or two or more together, may also find a useful application in other types of stethoscope constructions differing from the type discussed above.

While the invention has been illustrated and described as embodied in a stethoscope comprising a double-headed body contact piece having a non-differential auscultation head not provided with a diaphragm and a differential-auscultation head provided with an acoustic diaphragm, it is not intended to be limited to the particular details shown, since various modifications and structural changes may be made without departing in any way from the scope and spirit of the present invention.

Without further analysis, the foregoing will so fully reveal the gist of the present invention that others can, by applying present knowledge, readily adapt it for various applications without omitting features or aspects that, from the standpoint of prior art, fairly constitute essential characteristics of the generic or specific aspects of this invention.

What is claimed as new and desired to be protected by patent is set forth in the following claims.

1. A stethoscope comprising
 a double-headed body contact piece provided with first and second acoustic connector portions which are respectively connectable to first and second acoustic-signal-transmitting passages of a two-acoustic-passage stethoscope-tube attachment, the double-headed body contact piece comprising a first, non-differential auscultation head having a single auscultation chamber that is to be placed in acoustic communication with a surface of the body of a patient, the double-headed body contact piece furthermore comprising a second, differential-auscultation head having a pair of auscultation chambers which are to be placed simultaneously with each other in acoustic communication with the surface of said body of the patient with a predetermined spacing between the two chambers of the pair of chambers, the double-headed body contact piece furthermore comprising a switchover mechanism operative for establishing acoustic connections from predetermined ones of said auscultation chambers to said acoustic connector portions and for acoustically isolating said acoustic connector portions from predetermined ones of said auscultation chambers, and for acoustically isolating each chamber of said pair of chambers of said second head from said single chamber of said first head, the switchover mechanism being movable between a first setting establishing acoustic connections from the single chamber of the first, non-differential auscultation head to both said first and said second acoustic connector portions while acoustically isolating said single chamber of said first auscultation head from both the one and the other chamber of said pair of chambers of said second auscultation head, and a second setting establishing an acoustic connection from one chamber of said pair of chambers of said second head to one of the two acoustic connector portions and an acoustic connection from the other chamber of said pair of chambers of said second head to the other of the two acoustic connector portions, while acoustically isolating each of said pair of chambers of said second head from said single chamber of said first auscultation head.

2. A stethoscope as defined in claim 1, said switchover mechanism comprising a rotary switchover member which is located in between the first and second auscultation heads and which is mounted for rotation relative to the first and second heads between first and second rotated positions respectively corresponding to said first and second settings of said switchover mechanism.

3. A stethoscope as defined in claim 2, wherein the switchover member has at least a first control surface portion of a particular shape and wherein one of said first and second heads is provided with a portion having a second control surface portion having a shape corresponding to the shape of the first control surface portion, the first and second control surface portions each having a respective opening leading to a respective passage and being displaceable relative to each other upon relative rotation of the switchover member and the auscultation heads in such a manner that in one of said settings of said switchover mechanism the first and second control surface portions are in surface-to-surface engagement with each other and the respective openings are in register with each other in order to establish at least in part one of said acoustic connections whereas in the other of said settings of said switchover mechanism the respective openings in the first and second control surface portions do not register with each other.

4. A stethoscope as defined in claim 2, wherein said first and second acoustic connector portions of the double-headed body contact piece are provided on the rotary switchover member.

5. A stethoscope as defined in claim 4, wherein the rotary switchover member has a control surface portion provided with two openings each of which is in acoustic communication with a respective one of the first and second acoustic connector portions, and wherein the second, differential-auscultation head includes a control surface portion which is complementary to the control surface portion of the switchover member and which is in surface-to-surface sliding engagement with the control surface portion of the rotary switchover member and which, furthermore, is provided with two openings each of which leads to a respective passage leading to a respective one of the two auscultation chambers of the second head, and wherein, in said second setting of said switchover mechanism, the two openings in said control surface portion of said switchover member register with respective ones of the two openings in said control surface portion of the second head, whereas in said first setting of said switchover mechanism the two openings in said control surface portion of said switchover member do not register with the two openings in said control surface portion of the second head.

6. A stethoscope as defined in claim 5, wherein said control surface portions are both at least approximately planar.

7. A stethoscope as defined in claim 3, wherein said control surface portions are both at least approximately planar 8. A stethoscope as defined in claim 2, wherein the body contact piece includes a head-interconnecting portion which holds the first and second heads spaced from each other in an axial direction of the rotary switchover member and which connects the first a nd second heads to each other in such a manner that the first and second heads cannot rotate relative to each other, and wherein the switchover member is configured to at least in part surround the head-interconnecting portion and is mounted to rotate about the head-interconnecting portion.

9. A stethoscope as defined in claim 8, wherein said first and second acoustic connector portions of the double-headed body contact piece are provided on the rotatable switchover member, wherein the head-interconnecting portion has two passages which are both in acoustic communication with the single chamber of the first, non-differential auscultation head, wherein the switchover member has two spaced passages each of which is in acoustic communication with a single respective one of the first and second acoustic connector portions, and wherein, in said first setting of said switchover mechanism, the angular position of the switchover member relative to the head-interconnecting portion is such that said two spaced passages of the switchover member are in acoustic communication with said two passages of said head-interconnecting portion, to thereby establish said acoustic connections from the single chamber of the first head to both the first and the second acoustic connector portions provided on the switchover member.

10. A stethoscope as defined in claim 9,
said head-interconnecting portion having an outer peripheral surface portion,
said two passages of said head-interconnecting portion extending at least in part radially and terminating at said outer peripheral surface portion of the head-interconnecting portion,
said switchover member having a central internal passage defining an inner peripheral surface portion of the switchover member,
said two spaced passages of the switchover member extending at least in part radially and terminating at said inner peripheral surface portion of the switchover member,
and wherein, in said first setting of said switchover mechanism, the outer peripheral surface portion of the head-interconnecting portion and the inner peripheral surface portion of the switchover member are in surface-to-surface engagement at least at the locations at which said two passages of said head-interconnecting portion register with said two spaced passages of the switchover member.

11. A stethoscope as defined in claim 1,
wherein the double-headed body contact piece has a plurality of internal passages, these internal passages including
internal passages in the first and second heads, acoustically communicating with the single chamber of the first head and with each one of the pair of chambers of the second head, and
internal passages interiorly of the structure of the switchover mechanism,
and wherein said acoustic connections that are established between said chambers and said first and second acoustic connector portions in said first and second settings of said switchover mechanism are established as a result of different ones of said internal passages being in register or not being in register with one another,
and wherein said internal passages are located, dimensioned and oriented in such a manner that:
when said switchover mechanism is in said first setting, the acoustic connection from the single chamber of the first head to the first acoustic connector portion has a geometry which is at least equivalent to and has dimensions the same as the acoustic connection from the single chamber of the first head to the second acoustic connector portion, and
when said switchover mechanism is in said second setting, the acoustic connection from one chamber of said pair of chambers to the first acoustic connector portion has a geometry which is at least equivalent to and has dimensions the same as the acoustic connection from the other chamber of the pair of chambers to the second acoustic connector portion 12. A stethoscope as defined in claim 1,
wherein the first and second connector portions are spaced from each other in a predetermined direction and are configured mirror-symmetrical to each other with respect to a symmetry plane, said predetermined direction being normal to said symmetry plane,
and wherein, when said switchover mechanism is in said first setting, the acoustic connection from the single chamber of the first head to the first acoustic connector portion and the acoustic connection from the single chamber of the first head to the second acoustic connector portion are mirror-symmetrical to each other with respect to said symmetry plane and have the same dimensions,
and wherein, when said switchover mechanism is in said second setting, the acoustic connection from one chamber of said pair of chambers to the first acoustic connector portion and the acoustic connection from the other chamber of said pair of chambers to the second acoustic connector portion are mirror-symmetrical to each other with respect to said symmetry plane and have the same dimensions.

13. A stethoscope as defined in claim 12,
wherein said switchover mechanism comprises a switchover structure located in between said first and second heads of the double-headed body contact piece, the switchover structure being mounted for relative movement relative to said first and second heads,
and wherein said first and second acoustic connector portions are provided on said switchover structure.

14. A stethoscope as defined in claim 11,
wherein said switchover mechanism comprises a switchover structure located in between said first and second heads of the double-headed body contact piece, the switchover structure being mounted for relative movement relative to said first and second heads,
and wherein said first and second acoustic connector portions are provided on said switchover structure.

15. A stethoscope as defined in claim 2,
wherein said rotary switchover member has two axial end surfaces,
and wherein each of said first and second heads has at an axial end thereof which faces the switchover member a respective axial end surface,
at least one of the two axial end surfaces of the rotary switchover member being provided with a respective annular sealing ring confined between such axial end surface and the facing axial end surface of one of the two heads,
the first and second acoustic connector portions being provided on said rotary switchover member and the switchover member being provided with internal passages which are in acoustic communication with respective ones of the first and second acoustic connector portions and which terminate at and are open at predetermined locations on said at least one axial end surface of the rotary switchover member,
the annular sealing ring being located radially outwards of said predetermined locations.

16. A stethoscope as defined in claim 15,
wherein the sealing ring is made of polytetrafluoroethylene.

17. A stethoscope as defined in claim 1,
the switchover mechanism being provided with click-action detent means for causing the switchover mechanism to be arrested in a well-defined manner in each of the settings thereof.

18. A stethoscope as defined in claim 2,
the body contact piece having an exterior provided with visible indicia which indicate to a user whether the angular position of the rotary switchover member relative to the first and second heads is an angular position corresponding to the first setting or to the second setting.

19. A stethoscope as defined in claim 1, wherein the second, differential-auscultation head, at the axial end thereof which is to be placed against the surface of said body of the patient is provided with a diaphragm.

20. A stethoscope as defined in claim 1, wherein the first, non-differential auscultation head has a rim at the axial end thereof which is to be placed against the surface of said body of the patient, the rim being provided with a sealing ring which is made of elastomeric material and which is provided to engage the body of the patient.

21. A stethoscope as defined in claim 1, wherein the pair of chambers of the second, differential-auscultation head are each defined by a respective concave surface of spherical or paraboloidal geometry.

22. A stethoscope as defined in claim 21, wherein the respective concave surfaces of the pair of chambers have geometric centers or foci which are spaced by more than 10 mm.

23. A stethoscope as defined in claim 21, wherein the two chambers of said pair of chambers of the second head are not entirely discrete from each other but instead overlap into each other to a limited degree.

24. A stethoscope as defined in claim 1, wherein the first, non-differential auscultation head is of smaller diameter and the second, differential-auscultation head is of larger diameter.

25. A double-headed body contact piece for a stethoscope, comprising.
   a non-differential first auscultation head having a single auscultation chamber and having front and back ends,
   a differential second auscultation head having front and back ends, and having a pair of auscultation chambers which are to be placed simultaneously with each other in acoustic communication with a surface of the body of a patient with a predetermined spacing between the two chambers of said pair of chambers,
   a switchover member having a rotation axis which extends in a direction from said back end of said first head to said back end of said second head, a first control surface area, and a second control surface area,
   said first auscultation head having at said back end a first control surface which is complementary to and engages said first control surface area of said switchover member in surface-to surface sliding contact therewith,
   said second auscultation head having at said back end a second control surface which is complementary to and engages said second control surface are of the switchover member in surface-to-surface sliding contact therewith,
   said heads and member being provided with mounting means holding said switchover member between said first and second auscultation heads for joint rotation of said heads relative to said switchover member between at least a first angular setting and a second angular setting.
   said switchover member being provided with first and second acoustic connector portions, to respective ones of which two tubes of a double-tube stethoscope-tube attachment can be acoustically connected, said first and second acoustic connector portions being provided with respective first and second acoustic passages, said first and second acoustic passages extending into an interior of said switchover member, said single chamber of said first auscultation head including a central passage which extends in a direction towards said back end of said first head and is provided with first and second side passages which acoustically communicate with said central passage,
   said first angular setting being an angular setting in which each of said first and second side passages is in acoustical communication with a respective one of said first and said second acoustic passages,
   said first control surface are of said switchover member being so configured that, when said switchover member is rotated a sufficient angular distance away from said first setting, said first control surface are of said switchover member blocks off said first and second side passages and thereby acoustically isolates said single chamber of said first head from said first and from said second acoustic passages,
   said second auscultation head being provided with two openings, each opening being located at substantially a center of a respective one of said first and second chambers of said second head,
   said two openings each extending from the central portion of an interior of a respective one of said first and second chambers to said second control surface at said back end of said second head,
   said second angular setting being an angular setting in which each of said two openings of said second head is in acoustic communication with a respective one of said first and said second acoustic passages,
   said second control surface area of said switchover member being so configured that, when said switchover member is rotated a sufficient angular distance away from said second setting, said second control surface area of said switchover member blocks off said two openings of said second head and thereby acoustically isolates said first and second chambers of said second head from said first and second acoustic passages.

26. A double-headed body contact piece for a stethoscope, comprising
   a non-differential first auscultation head having a single auscultation chamber and having front and back ends,
   a differential second auscultation head having front and back ends, and having a pair of auscultation chambers which are to be placed simultaneously with each other in acoustic communication with a surface of the body of a patient with a predetermined spacing between the two chambers of said pair of chambers,
   a switchover member having a rotation axis, a first control surface are, and a second control surface area,
   said first auscultation head having at said back end a first control surface which is complementary to and engages said first control surface area of said switchover member in surface-to-surface sliding contact therewith, said second auscultation head having at said back end a second control surface which is complementary to and engages said second control surface area of the switchover member in surface-to-surface sliding contact therewith, said heads and member being provided with mounting means holding said switchover member between said first and second auscultation heads for joint rotation of said heads relative to said switchover member between at least a first angular setting and a second angular setting, said switchover member being provided with first and second acoustic connector portions, to respective ones of two tubes of a double-tube stethoscope-tube attachment that can be acoustically connected, said first and second acoustic connector portions being provided with respective first and second acoustic passages, said first and second acoustic passages extending for equal distances into an interior of said switchover member at opposite respective sides of said rotation axis of said switchover member at equal radial distances from said rotation axis and at equal axial positions, said single chamber of said first auscultation head including a central passage which extends in a direction towards said back end of said first head and is provided with first and second side passages, said first and second side passages acoustically communicating with said central passage at respective locations which are equally spaced in the axial direction from said front end of said first head, said first and second side passages extending to and said first control surface, and at said first control surface being positioned at opposite sides of said rotation axis of said switchover member at equal redial distances from said rotation axis, said first angular setting being an angular setting such that a line joining said first and second side passages at said first control surface forms equal angles with a direction in which said first acoustic passage extends and with a direction in which said second acoustic passage extends, with each of said first and second side passages being in acoustic communication with a respective one of said first and said second acoustic passages, said first control surface area of said switchover member being so configured that, when said switchover member is rotated a sufficient angular distance away from said first setting, said first control surface area of said switchover member blocks off said first and second side passages and thereby acoustically isolates said single chamber of said first head from said first and from said second acoustic passages, said second auscultation head being provided with two openings, each opening being located at substantially the center of a respective one of said first and second chambers of said second head, said two openings each extending from the central portion of an interior of a respective one of said first and second chambers to said second control surface at said back end of said second head, said chambers of said second head being so located that said two openings are, at said second control surface, located at opposite sides of said rotation axis at equal radial distances from said rotation axis, said second angular setting being an angular setting such that a line joining said two openings of said second head at said second control surface forms equal angles with the direction in which said first acoustic passages extends and with the direction in which said second acoustic passage extends, with each of said two openings of said second head being in acoustic communication with a respective one of said first and said second acoustic passages, said second control surface are of said switchover member being so configured that, when said switchover member is rotated a sufficient angular distance away from said second setting, said second control surface area of said switchover member blocks off said two openings of said second head and thereby acoustically isolates said first and second chambers of said second head from said first and second acoustic passages.

27. A body contact piece as defined in claim 26,
wherein said first and second side passages, occupy at said first control surface positions which are diametrically opposite to each other relative to said rotation axis of said switchover member.

28. A body contact piece as defined in claim 26,
wherein said first and second acoustic passages extend into the interior of said switchover member parallel to each other, wherein said first and second side passages, occupy at said first control surface of said first head positions which are diametrically opposite to each other relative to said rotation axis of said switchover member, so that in said first angular setting, considered at said first control surface, a line joining said first and second side passages at said first control surface extends perpendicular to the direction in which said first and second acoustic passages extend.

29. A body contact piece as defined in claim 28,
wherein said two openings of said second head are, at said second control surface at said back end of said second head, located diametrically opposite to each other relative to the rotation axis of said switchover member, so that in said second angular setting, at said second control surface at said back end of said second head, a line joining said two side openings extends perpendicular to the direction in which said first and second acoustic passages extend.

30. A body contact piece as defined in claim 26,
wherein said first and second acoustic passages extend into the interior of said switchover member parallel to each other, wherein said two openings of said second head are, at said second control surface at said back end of said second head, located diametrically opposite to each other relative to the rotation axis of said switchover member, so that in said second angular setting, at said second control surface at said back end of said second head, a line joining said two openings extends perpendicular to the direction in which said first and second acoustic passages extend.

31. A body contact piece as define in any one of claims 25-30,
wherein said switchover member is furthermore provided with two axial passages each commencing at said second control surface area of said switchover member and extending generally axially at least part of the way to said first control surface area of said switchover member, each of said two axial passages intersecting a respective one of said first and second acoustic passages so as to be in permanent acoustical communication with the respective one of said acoustic passages, said two axial passages having radial and angular locations such that in said first angular setting each of said first and second side passages is in acoustic communication with a respective one of said first and second acoustic passages through an intermediary of a respective one of said two axial passages whereas said two openings of said second head are blocked off by reason of failure to communicate with either of said two axial passages.

32. A body contact piece as defined in any one of claims 25-30,
wherein said switchover member is furthermore provided with two radial openings each of which is in permanent acoustical communication with a respective one of said first and second acoustic passages and each of which extends, with a generally radial orientation, to said first control surface area of said switchover member, said two radial openings having axial and angular locations such that in said first angular setting each of said first and second side passages is in acoustical communication with a respective one of said first and second acoustic passages through an intermediary of a respective one of said two radial openings whereas, when said switchover member is moved a sufficient angular distance away from said first angular setting, said first and second side passages are blocked off by reason of failure to communicate with either of said two radial openings.

33. A body contact piece as defined in any one of claims 25-30,
wherein said switchover member is furthermore provided with two axial passages each commencing at said second control surface are of said switchover member and extending generally axially at least part of the way to said first control surface area of said switchover member, each of said two axial passages intersecting a respective one of said first and second acoustic passages so as to be in permanent acoustical communication with the respective one of said acoustic passages, wherein said switchover member is furthermore provided with two radial openings each of which commences at said firs control surface area of said switchover member and extends away therefrom with a generally radial orientation to intersect and thus be in permanent acoustical communication with a respective one of said two axial passages so as to be furthermore in permanent acoustical communication with a respective one of said first and second acoustic passages, said two axial passages having radial and angular locations and said two radial openings having axial and angular locations; such that:
in said first angular setting:
each of said first and second side passages is in acoustic communication with a respective one of said two radial openings and thus in acoustical communication with a respective one of said two axial passages and thus furthermore in acoustical communication with a respective one of said first and second acoustic passages, whereas said two openings of said second head are blocked off by reason of failure to communicate with either of said two axial passages, and in said second angular setting:
each of said two openings of said second head is in register with and thus in acoustical communication with a respective one of said two axial passages and thus in acoustical communication with a respective one of said first and second acoustic passages, whereas said first and second side passages are blocked off by reason of failure to communicate with either of said two radial openings of said switchover member.

34. A body contact piece as defined in any one of claims 25-30,
said switchover member having generally planar first and second axial end surfaces and a central cylindrical bore, said first control surface area of said switchover member being at least in part formed by said first axial end surface and a peripheral surface of said central cylindrical bore, and said second control surface area being at least in part formed by said second axial end surface, said first auscultation head including a front part having a front end adapted to be placed against the surface of said body of the patient and a back end, and furthermore including a generally cylindrical back part located generally centrally at said back end of said front part and extending axially away therefrom, said back end of said front part having an annular generally planar surface which engages said first axial end surface of said switchover member in sliding contact therewith, said generally cylindrical back part of said first head extending into said central cylindrical bore of said switchover member with an outer periphery of said generally cylindrical back part engaging the periphery of said central cylindrical bore in sliding contact therewith, said first control surface of said first head being at least in part formed by said annular generally planar surface and said outer periphery of said back part, said second auscultation head having a front end adapted to be placed against the surface of said body of the patient and having a generally planar back end whose surface at least in part forms said second control surface and engages said generally planar second end surface of said switchover member in sliding contact therewith, said back part of said first head being non-rotatable relative to said front part of said first head and extending through said central bore of said switchover member at least to reach said back end of said second head and being mechanically connected to the second head for joint rotation of said first and second heads.

35. A body contact piece as defined in claim 34,
wherein said switchover member is furthermore provided with two radial openings, each being located axially inward of said first axial end surface of said switchover member at the peripheral surface of said central cylindrical bore of said switchover member, each of said two radial openings being in permanent acoustic communication with a respective one of said first and second acoustic passages, said two radial openings having angular locations such that in said first angular setting each of said first and second side passages is in acoustical communication with a respective one of said first and second acoustic passages through an intermediary of a respective one of said two radial openings whereas, when said switchover member is moved a sufficient angular distance away from said first angular setting, said first and second side passages are blocked off by reason of failure to communicate with either of said two radial openings.

36. A body contact piece as defined in claim 34, wherein said switchover member is furthermore provided with two axial passages each commencing at said generally planar second axial end surface of said switchover member and extending generally axially at least part of the way to said generally planar first axial end surface of said switchover member, each of said two axial passages intersecting a respective one of said first and second acoustic passages so as to be in permanent acoustical communication with the respective one of said acoustic passages, wherein said switchover member is furthermore provided with two radial openings, each being located axially inward of said first axial end surface of said switchover member at the peripheral surface of said central cylindrical bore of said switchover member, each of said two radial openings extending away from said peripheral surface of said central cylindrical bore with a generally radial orientation and intersecting and thus being in permanent acoustical communication with a respective one of said two axial passages so as to be furthermore in permanent acoustical communication with a respective one of said first and second acoustic passages, said two axial passages having radial and angular locations and said two radial openings having angular locations such that:

in said first angular setting:
each of said first and second side passages is in acoustic communication with a respective one of said two radial openings and thus in acoustical communication with a respective one of said two axial passages and thus furthermore in acoustical communication with a respective one of said first and second acoustic passages,
whereas said two openings of said second head are blocked off by reason of failure to communicate with either of said two axial passages, in said second angular setting:
each of said two openings of said second head is in register with and thus in acoustical communication with a respective one of said two axial passages and thus in acoustical communication with a respective one of said first and second acoustic passages,
whereas said first and second side passages are blocked off by reason of failure to communicate with either of said two radial openings of said switchover member.

37. A body contact piece as defined in claim 35, said two radial opening having the same axial locations.

38. A body contact piece as defined in claim 36, said two radial openings having the same axial locations.

* * * * *